(12) United States Patent
Schoolman

(10) Patent No.: US 6,415,792 B1
(45) Date of Patent: Jul. 9, 2002

(54) ANESTHESIA MACHINE WITH HEAD WORN DISPLAY

(75) Inventor: Arnold Schoolman, Kansas City, MO (US)

(73) Assignee: Schoolman Scientific Corporation, Kansas City, MO (US)

( * ) Notice: Subject to any disclaimer, the term of this patent is extended or adjusted under 35 U.S.C. 154(b) by 0 days.

(21) Appl. No.: 08/523,535

(22) Filed: Sep. 5, 1995

Related U.S. Application Data

(62) Division of application No. 08/419,907, filed on Apr. 11, 1995, now abandoned.

(51) Int. Cl.[7] .............................................. A61M 16/01
(52) U.S. Cl. .............................. 128/204.23; 128/203.12; 128/205.23
(58) Field of Search ..................... 345/8, 9; 364/413.02, 364/413.03; 128/671, 202.22, 203.12, 203.14, 204.21, 204.23, 205.23

(56) References Cited

U.S. PATENT DOCUMENTS

| | | | |
|---|---|---|---|
| 4,383,534 A | * 5/1983 | Peters .................... | 128/207.15 |
| 4,737,972 A | 4/1988 | Schoolman ................ | 378/41 |
| 5,003,300 A | 3/1991 | Wells ........................ | 340/705 |
| 5,231,981 A | 8/1993 | Schreiber et al. ......... | 128/205.23 |
| 5,301,668 A | 4/1994 | Hales ..................... | 128/205.23 |

* cited by examiner

*Primary Examiner*—Eric F. Winakur
(74) *Attorney, Agent, or Firm*—John C. McMahon

(57) ABSTRACT

An anesthesia machine with a head worn display includes a gas delivery system and a patient monitor system cooperating in such a manner as to monitor the anesthesia and vital parameters of a patient in surgery. The gas delivery system supplies oxygen or a gaseous anesthetic at a controlled pressure and flow rate as monitored by gas delivery sensors. The gas delivery sensors and patient vital parameter sensors are interfaced to a monitor processor and the measured values of the sensors can be displayed on a head worn display device having stereoscopic capabilities. The monitor processor includes communication ports for selectively monitoring the sensors of a similar anesthesia machine remotely positioned and for downloading patient medical records from a hospital medical records computer. A wireless communication link can be employed between the monitor processor and the head worn display to facilitate movement of an anesthesiologist about an operating room.

7 Claims, 3 Drawing Sheets

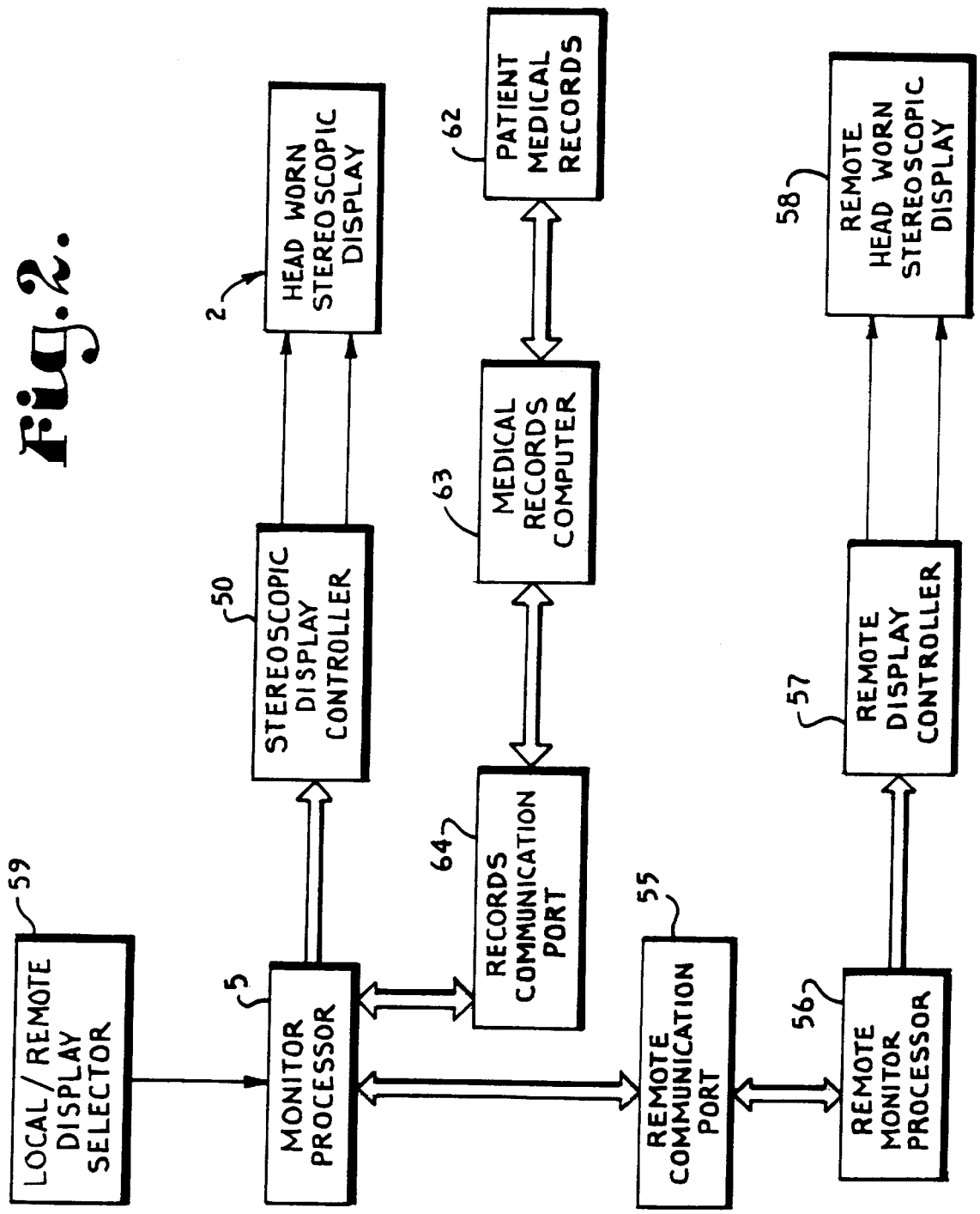

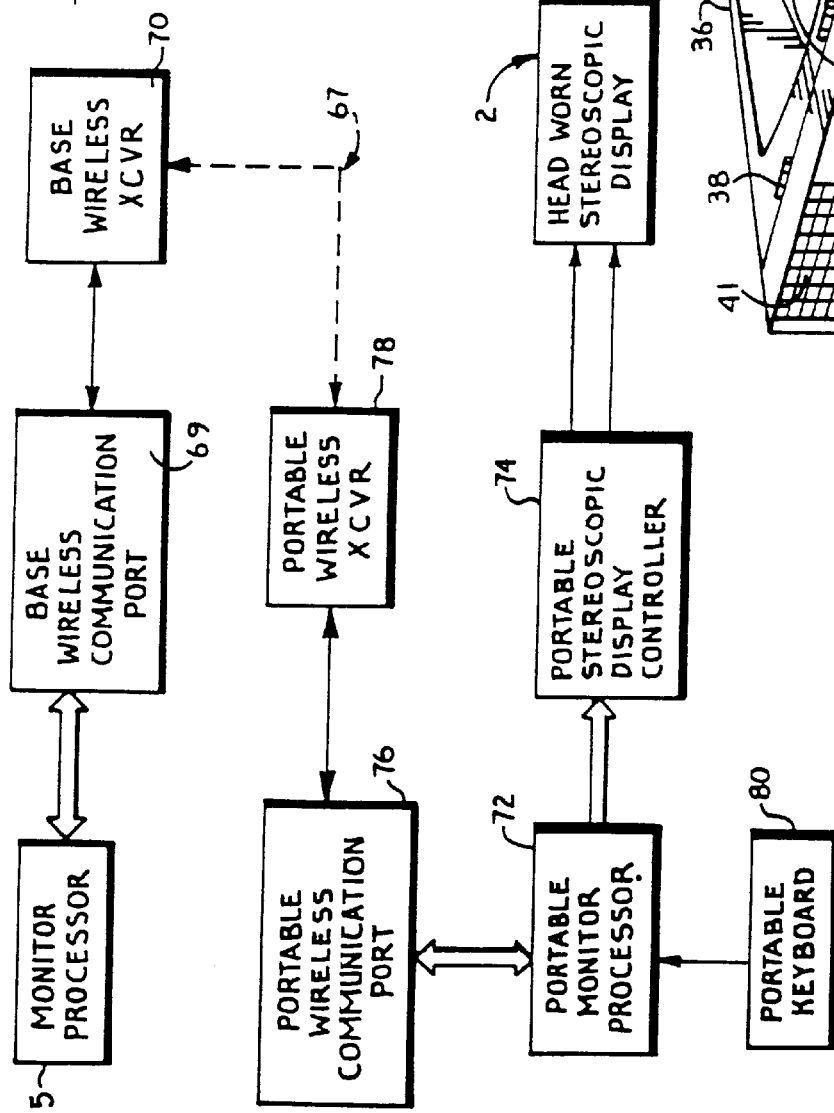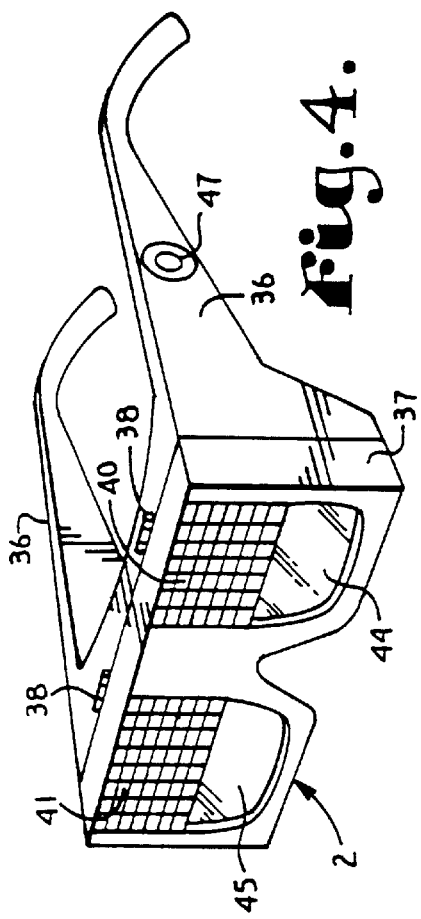

ANESTHESIA MACHINE WITH HEAD WORN DISPLAY

CROSS-REFERENCE TO RELATED APPLICATIONS

This is a divisional application of U.S. Ser. No. 08/419,907 filed Apr. 11, 1995 entitled an ANESTHESIA MACHINE WITH HEAD WORN DISPLAY, now abandoned.

BACKGROUND OF THE INVENTION

During major surgeries in which general anesthesia is used, it is necessary to monitor the vital functions of the anesthetized patient and additionally to control and monitor the anesthesia process. Systems referred to as "anesthesia machines" have been developed to facilitate such control functions of the anesthesia delivery and some of the monitoring functions thereof. The anesthesia machine provides controls for the flow and mixtures of oxygen and a gaseous anesthetic to the patient with gauges or indicators for monitoring the flow rates and supply pressures. Modern anesthesia machines are equipped with spirometers that measure respiratory volumes within the breathing circuit, ventilators with disconnect alarms, waste gas scavengers, and oxygen analyzers. Humidifiers and nebulizers are available that connect between the anesthesia machine and the breathing circuit. Vital parameters which are monitored and indicated include patient temperature, blood pressure, pulse rate, oxygen and carbon dioxide concentrations and electrocardiographic data.

In the modern day practice of anesthesiology, computers not only facilitate monitoring traditional variables such as blood pressure, heart rate, and electrocardiogram, they also allow the monitoring of variables which could not otherwise be monitored. For example, the use of cardiac output monitors is now commonplace. The monitoring of less available indicators of lung function using computers is now a reality. A lung-water computer can monitor the extra vascular lung water, and real-time monitoring of respiratory gas exchange can be readily accomplished.

Computer processing of the electroencephalogram (EEG) has transformed a complicated chart-oriented activity performed only by neurologists into a real-time monitoring function performed easily during surgical procedures. Computer analysis of the EEG continues to improve and now compares favorably with visual evaluation. Computerized EEG monitoring is beneficial in the analysis of anesthetic effects. EEG analysis is also useful in ascertaining the specific effects of various drugs and anesthetic techniques on cerebral activity. Although the monitoring of the depth of anesthesia has remained an elusive goal, work in this field is showing promise.

Because of the increasing complexity of monitoring equipment, computers have also been employed for analysis and calibrations. For example, complicated mass spectrometers, used in the analysis of gas concentrations in operating rooms are calibrated easily without time consuming human intervention. Alternatives in monitoring methods can be evaluated comprehensively with the aid of computers for selection of the best of possible monitoring choices depending of the circumstances at hand.

Technology in general and computers in particular are providing anesthetists with more information about what is happening to their patients. Computers have been and continue to be of great value in interpreting what is an increasingly complex process of physiological monitoring.

Because of the increasing number of functions and parameters which must be monitored by the anesthetist, the potential exists for information overload in which critical changes in parameters can be missed because of the volume of information which must be monitored. Complicating the situation is that with convention al equipment, the readouts and indicators may be distributed about the operating room and, therefore, difficult to scan visually and locate quickly from the anesthetist's position at the head of the operating table facing the patient. The anesthetist must occasionally make adjustments to the anesthetic and oxygen flow control, intravenous lines, and monitoring equipment which sometimes requires movement away from the head of the operating table and subsequent reorientation to the monitor readouts.

Training and the upgrading and sharpening of skills are constant processes in the medical arts in general. There is also a trend toward the transitioning of many skilled functions away from physicians to technicians and nurses under the supervision of physicians. In anesthesiology, nurse anesthetists are employed for many surgical procedures. Currently, it is often impractical for an anesthesiologist to adequately supervise multiple nurse anesthetists or anesthesiologists in training in simultaneous operations because of the physical layout of a surgical department of a hospital.

SUMMARY OF THE INVENTION

The present invention provides an improved anesthesia machine in which the machine function parameters and patient vital parameters are displayed in a coordinated manner on a single display device which has stereoscopic capabilities. The present invention is intended to be capable of communicating with a medical records computer which stores records of the medical history and test results of a patient for quick access during surgical operations. The patient monitor of the anesthesia machine of the present invention additionally has the capability of communicating with other similar anesthesia machines to selectively display the monitored functions thereof to enable a senior anesthesiologist to supervise anesthesiologists and anesthetists remotely.

The anesthesia machine of the present invention includes a gas delivery system cooperating with a computerized patient monitor system. The gas delivery system includes sources of pressurized oxygen and an anesthesia gas, a gas flow control for each gas, a pressure sensor for each gas source, and a flow sensor for each gas.

The patient monitor system includes a plurality of patient vital parameter sensors, such as temperature, heart rate, blood pressure, a blood flow transducer, an electrocardiogram transducer, an electroencephalogram transducer, blood gas sensors, and the like. A digital monitor processor or central processing unit has one or more monitor communication ports interfaced thereto, to which are interfaced the various vital parameter sensors and gas delivery sensors. Depending on the nature of the particular sensor, an analog to digital converter may be incorporated into the sensor. The sensor assemblies may be interfaced to the monitor ports using a single line per sensor or multiple lines of the ports, again depending on the nature of the sensor. The monitor processor includes conventional peripheral devices, such as a keyboard/trackball unit for data and command input, memory such as RAM and ROM, mass storage devices such as a hard drive and/or CDROM or other optical storage device, a printer, and a display subassembly.

The display subassembly of the anesthesia machine of the present invention includes a stereoscopic display controller and a head worn color stereoscopic display which preferably includes a set of left and right color liquid crystal displays (LCD's). Although the majority of displayed data will be alphanumeric and not benefit from stereoscopic display, some types of graphic data might be more clearly presented stereoscopically. Preferably, a conventional color monitor or cathode ray tube is also connected to the display controller for viewing by other personnel in the operating room, such as the surgeons, nurses, and technicians. A sound controller interfaced to the monitor processor has a microphone and speaker and/or earphone connected thereto and allows digital recording of verbal notes of the anesthesiologist during the operation.

The monitor processor preferably includes a records communication port for quick access to the patient's medical records from a medical records computer of the hospital during the operation. The records communication port may, for example, be a local area network interface. The parameters measured during an operation, and the digitized anesthesiologists verbal notes, are preferably recorded on the mass storage device and may be periodically uploaded to the medical records computer for subsequent analysis and follow-up or for training purposes.

In order to enable a senior anesthesiologist to supervise anesthesiologists in training or nurse anesthetists, the monitor processor preferably includes a remote communication port interfaced to a remote patient monitor processor of a remote anesthesia machine similar to one described above. A local/remote display selector is provided on the main monitor processor and may be in the form of displayed indicia which may be selected using the keyboard or trackball.

The head worn display of the anesthesia machine of the present invention has the capability of receiving its display signal wirelessly to facilitate the performance of the anesthesiologist. The preferred wireless link is based on radio transceivers, although the use of an infrared link is also contemplated. A portable monitor processor has a portable display controller with stereoscopic capabilities interfaced thereto which drives the head worn display. A portable keyboard providing for data and command entry is interfaced to the portable processor. All the components of the portable display system except for the head worn display and a small antenna or set of antennas may be housed in the portable keyboard. The wireless link is at least duplex to simultaneously carry a display signal from the base monitor processor to the portable display device and to carry data and command entries from the portable keyboard to the base monitor processor. The left and right display channels of a stereoscopic display signal may conceivably be multiplexed onto a single display signal or alternatively, separate left and right display wireless channels may be employed.

OBJECTS AND ADVANTAGES OF THE INVENTION

The principal objects of the present invention are: to provide an improved apparatus for monitoring anesthetized patients during surgical operations; to provide particularly an anesthesia machine including a computerized patient monitor system with all monitored functions displayed on a display device worn on the head of the anesthesiologist; to provide such a machine including a gas delivery system for oxygen and anesthetic gases including pressurized gas sources in the form of portable tanks or connections to hospital central gas supplies, gas flow controls, gas source pressure sensors, and gas flow sensors; to provide such a machine including a plurality of patient vital parameter sensors such as transducers for measuring temperature, heart rate, blood pressure, blood flow, electrocardiographic data, electroencephalographic data, blood gas concentrations, and the like; to provide such a machine including a monitor processor having the gas delivery sensors and vital parameter sensors interfaced thereto; to provide such a machine including a stereoscopic display controller and a head worn stereoscopic display with a set of left and right color LCD's; to provide such a machine including the capability of connection of a conventional video display monitor to the display controller for viewing by other personnel in an operating room; to provide such a machine including a communication interface to a hospital medical records computer for quick access to patient medical records during an operation; to provide such a machine including a communication interface to similar anesthesia machines in other operating rooms for supervision of a plurality of anesthesiologists and anesthetists by a senior anesthesiologist; to provide such a machine including a wireless link between the anesthesia machine and the head worn display to enable an anesthesiologist to move more freely about an operating room; and to provide such an anesthesia machine with a head worn display which is economical to manufacture, which is convenient in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a block diagram illustrating connection of the monitor processor of the anesthesia machine to a remote monitor processor and to a patient medical records computer.

FIG. 3 is a block diagram illustrating the use of a wireless link between the monitor processor of the anesthesia machine and the head worn display thereof.

FIG. 4 is a perspective view of an exemplary head mounted stereoscopic display device for use with the anesthesia machine of the present invention.

DETAILED DESCRIPTION OF THE INVENTION

Figure 1:
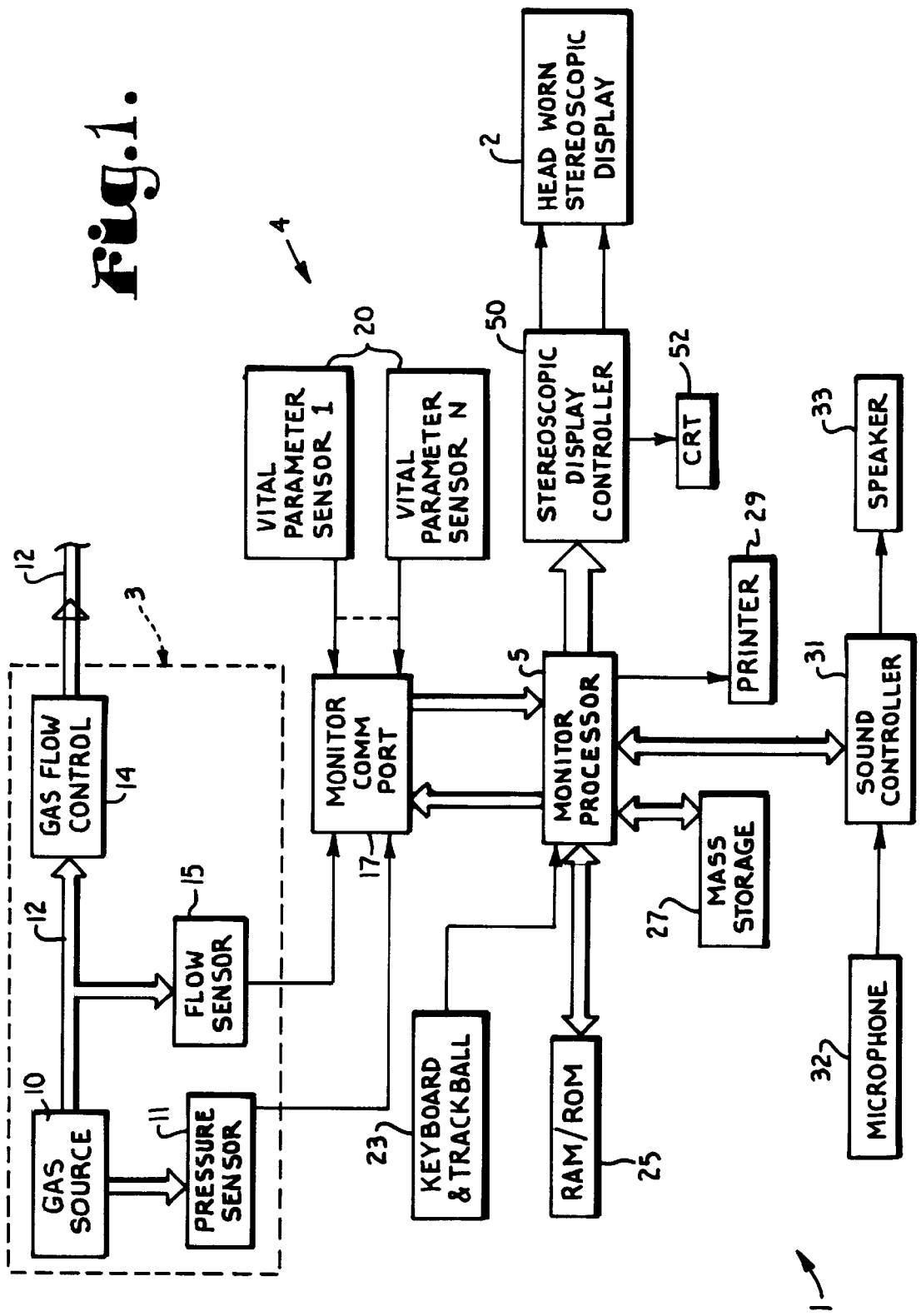
FIG. 1 is a block diagram illustrating the principal components of an anesthesia machine with a head worn display according to the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates an anesthesia machine with a head worn display device 2 which embodies the present invention. The machine 1 generally includes a gas delivery and monitor system 3 and a patient monitor system 4. The patient monitor system 4 includes a digital processor 5 which coordinates the display of the monitored parameters on the display device 2.

The gas delivery and monitor system 3 is in many respects a conventional type of apparatus which is referred to as an anesthesia machine. The gas system 3 provides for the controlled flow of gases such as oxygen and a gaseous anesthetic to a surgical patient and includes sensors for monitoring such gas flow. Because such apparatus is generally well known, a very simplified diagram of such a gas system 3 is illustrated in FIG. 1. Although intravenous anesthetics are sometimes used during surgeries, in almost all cases, oxygen is supplied to the anesthetized patient. Only a single gas circuit is shown in FIG. 1; however, those skilled in the art will recognize that additional gas circuits may be present and may be accommodated by the machine 1.

The illustrated gas system 3 includes a pressurized gas source 10 which may include a central gas supply of a hospital, portable gas tanks, or a combination of the two. A gas pressure sensor 11 senses the source pressure. A gas delivery conduit 12 has a gas flow control 14 therein which may take the form of a rotary throttle valve for manual operation or, alternatively, remotely controlled powered operation. A gas flow sensor 15 is connected to the conduit 12 and measures the volume flow of the gas to the patient. Although not shown, the conduit 12 would have one or more pressure regulators upstream of the control 14. The sensors 11 and 15 include analog transducers and incorporate analog to digital converters (not shown) which convert the measured gas delivery parameters to binary numbers for reading by the processor 5. The processor 5 includes a monitor communication port 17 which interfaces the sensors 11 and 15 to the processor 5.

The patient monitor system 4 includes a plurality of patient vital parameter sensors 20, which are illustrated as sensor 1 through sensor N. The sensors 20 include transducers for measuring a number of patient vital signs or parameters, such as temperature, heart rate, blood pressure, blood flow rate, blood gas concentrations, electrocardiographic and electroencephalographic data, and the like. Not all procedures require monitoring all such parameters, and some require that more parameters be monitored. As with the gas sensors 11 and 15, the vital sensors 20 incorporate analog to digital converters (not shown) which convert the measured values to binary numeric data for reading by the processor 5. The vital sensors 20 are interfaced to the processor 5 by way of the monitor communication port 17.

Preferably, the monitor processor 5 is a high performance microprocessor such as a Pentium (Intel), a Power PC (Motorola), or the like. The processor 5 has a keyboard/trackball unit 23 interfaced thereto for the entry of data and commands. A large amount of efficient read/write memory or RAM is interfaced to the processor 5 along with a ROM unit storing low level input and output routines. The RAM and ROM are combined in a single box labeled RAM/ROM 25 in FIG. 1. An operating system, application programs, and data from the sensors 11, 15, and 20 are stored in a mass storage device 27 which includes a large, high speed hard disk drive and may also include read/write and/or read-only optical mass storage devices, such as WORM drives, CDROM drives, and the like. A printer 29 is interfaced to the processor 5 for generating hard copies of data from the processor 5, including periodic readings from the sensors 11, 15, and 20.

A sound controller 31 is interfaced to the processor 5 and has a microphone 32 and a speaker or earphone 33 connected thereto. The sound controller 32 may be a multichannel device which enables simultaneous recording of digitized verbal notes and the playback of stored files representing alert or alarm signals to be played when selected ones of the sensors 11, 15, or 20 measure values move outside of ranges considered safe. Additionally, the speaker 33 allows previously stored voice notes to be played back.

The head worn stereoscopic display 2 is illustrated in FIG. 4 as having the form of a pair of spectacles, although other configurations are contemplated, such as disclosed in U.S. Pat. No. 4,737,972 referenced above and U.S. Pat. No. 5,281,957 issued to the present inventor on Jan. 25, 1994 which is incorporated herein by reference. The illustrated display 2 includes a temple frame 36 with a display frame 37 hingedly connected thereto by hinge members 38. A left LCD 40 and a right LCD 41 are mounted on the display frame 37. Preferably, the LCD's 40 and 41 are high resolution color LCD's and may be either passively backlit or may incorporate backlighting panels (not shown). Close focus optics (not shown) are provided to enable comfortable viewing of the LCD units 40 and 41 when the display device 2 is positioned on the head of a viewer.

The display device 2 has the form of bifocals in that below each LCD 40 and 41 is an associated lens 44 and 45 which may be ground to prescription lenses for the wearer. The display frame 37 may be flipped up to provide unrestricted viewing without removing the head worn display 2. A jack 47 may be provided on the structure of the display 2 for connection of a cable from a display controller 50 to carry display signals from the monitor processor 5 to the LCD's 40 and 41. Additional provisions may be made for mounting the microphone 32 and an earphone 33 on the temple frame 36. Alternatively, the microphone 32 and earphone 33 may form a separate unit from the display device 2.

The display controller 5 is interfaced to the monitor processor 5 and receives data therefrom for display on the head worn display device 2. The display controller 5 generates a display signal which represents the image to be displayed. The controller has stereoscopic capabilities for displaying graphic images which can be more clearly presented with the added dimension of depth provided by stereoscopy. In most cases, monoscopic display, particularly of alphanumeric data and two dimensional waveforms, is adequate and requires less processing overhead from the processor 5 and controller 50. In the case of a monoscopic display, the left and right display signals are identical. The display controller 50 preferably has the capability of providing a monoscopic display signal to a conventional video display monitor or cathode ray tube (CRT) 52 for viewing by personnel in the operating room other than the anesthesiologist, such as surgeons, nurses, technicians, and the like. Such a monitor 52 may be a large screen monitor, such as a nineteen or twenty-one inch diagonal monitor.

The anesthesia machine 1 of the present invention has provisions for enabling an anesthesiologist in one operating room to supervise anesthesiologists or anesthetists in other operating rooms using similar anesthesia machines. Referring to FIG. 2, the monitor processor 5 has a remote communication port 55 which is interfaced to a remote monitor processor 56 having a remote display controller 57 and a remote head worn stereoscopic display 58 interfaced thereto. A local/remote display selector 59 of the processor 5 enables the anesthesiologist to view the locally monitored sensors 11, 15, and 20 on the display device 2 or parameters measured by sensors (not shown) interfaced to the remote processor 56 by causing the remote processor 56 to upload the display data through the port 55 to the local processor 5. The display selector 59 may be a particular key combination on the keyboard 23 or may take the form of an indicia displayed on the display device 2 which may be selected using the keyboard or trackball 23.

The anesthesia machine 1 also has the capability of providing quick access to patient medical records 62 stored in a medical records computer 63 of a hospital by way of a records communication port 64. The port 64 may take the form of a local area network interface. For quickest access to such records 62, the records may be downloaded from the computer 63 and stored on the local mass storage device 27 of the machine 1 prior to the surgical operation.

In order to provide an anesthesiologist wearing the display device 2 with the greatest physical freedom to move about the operating room, the anesthesia machine 1 can be provided with a wireless link 67 between the monitor processor 5 and the display device 2. Referring to FIG. 3, the monitor processor 5 is provided with a base wireless communication port 69 and a base wireless transceiver 70. A portable monitor processor 72 is interfaced by a portable stereoscopic display controller 74 to the display device 2. The processor 72 has a portable wireless communication port 76 which is connected to a portable wireless transceiver 78. A portable keyboard or keyboard/trackball unit 80 is interfaced to the processor 72 for the entry of data and commands. Data representing a display signal is sent from the processor 5 over the wireless link 67 to the display device 2, and data and commands originating from the portable keyboard 80 are sent by way of the portable processor 72 and the wireless link 67 back to the processor 5. All of the portable components except for the display device 2 and an antenna (not shown) may be mounted within the portable keyboard 80, which may include means such as a belt clip (not shown) for convenient carrying of the keyboard 80.

The wireless link 67 is preferably implemented as a radio communication link using frequencies in the 900 megahertz or 2.4 gigahertz range. Wireless LAN protocols may be employed to economize by using or adapting existing hardware and software routines. Radio frequencies are preferred for the wireless link 67 because of the ability of radio waves to penetrate many types of objects and, thus, are less likely to be blocked by structures within the operating room. However, the use of an infrared wireless link is also contemplated. The link 67 requires at least two channels, one in each direction between the processors 5 and 72. The left and right channels of the display signal can conceivably be multiplexed onto a composite display signal occupying a single channel. Alternatively, the left and right display signal components can be carried on separate channels.

It is to be understood that while certain forms of the present invention have been illustrated and described herein, it is not to be limited to the specific forms or arrangement of parts described and shown.

What is claimed and desired to be secured by Letters Patent is as follows:

1. An anesthesia apparatus comprising:
   (a) a gas delivery assembly adapted for delivering a selected gas to a patient;
   (b) a gas delivery control connected to and cooperating with said gas delivery assembly to control a flow volume of said selected gas to a patient;
   (c) a gas delivery sensor cooperating with said gas delivery assembly and sensing a gas parameter indicative of said flow volume of said selected gas and generating a gas parameter signal representing a value of said gas parameter;
   (d) a patient monitor assembly including at least one patient vital parameter sensor sensing a selected patient vital parameter and generating a patient parameter signal representing a value of said selected patient vital parameter;
   (e) a digital patient monitor processor having said gas delivery sensor and said patient parameter sensor interfaced thereto, said digital patient monitor processor executing a program to process data and generating alphanumeric and graphic data;
   (f) a display controller interfaced to said digital patient monitor processor and generating a display signal representing alphanumeric and graphic data generated by said digital patient monitor processor including indicia representing said gas parameter and said patient vital parameter; and
   (g) a head worn display device interfaced to said display controller, receiving said display signal, and displaying said alphanumeric and graphic data.

2. An apparatus as set forth in claim 1 and including:
   (a) a keyboard interfaced to said digital patient monitor processor.

3. An apparatus as set forth in claim 1 and including:
   (a) a communication port interfaced to said digital Patient monitor processor; and
   (b) said communication port being interfaced to a patient medical records computer storing patient medical records.

4. An apparatus as set forth in claim 1 and including:
   (a) a communication port interfaced to said digital patient monitor processor;
   (b) said communication port being selectively activated to interface said digital patient monitor processor to a remote processor of a remote anesthesia machine, said remote processor outputting a remote display signal; and
   (c) a display source selector interfaced to said digital patient monitor processor and enabling selection between said display signal from said digital patient monitor processor and said remote display signal from said remote processor.

5. An apparatus as set forth in claim 1 and including:
   (a) a plurality of patient vital parameter sensors, each sensor sensing an associated patient vital parameter, being interfaced to said digital patient monitor processor, and selectively causing display of indicia on said head worn display device of a value of the vital parameter associated with said sensor.

6. An apparatus as set forth in claim 1 and including:
   (a) a conventional video display device enabling viewing of images displayed thereon by multiple personnel, said conventional video display device being interfaced to said display controller.

7. An apparatus as set forth in claim 1 wherein:
   (a) said display controller outputs a stereoscopic display signal representing stereoscopic graphics; and
   (b) said head worn display device is stereoscopic.

* * * * *